United States Patent [19]  [11] Patent Number: 4,978,298
Eliasz                                [45] Date of Patent: Dec. 18, 1990

[54] DENTAL MOLDING PROCESS

[76] Inventor: Michael R. Eliasz, 8215 Westchester, Ste. 145, Dallas, Tex. 75225

[21] Appl. No.: 342,248

[22] Filed: Apr. 20, 1989

[51] Int. Cl.⁵ .................................................. A61C 11/00
[52] U.S. Cl. .................................... 433/213; 433/214
[58] Field of Search .................. 433/213, 214; 264/16, 264/17, 18

[56] References Cited

U.S. PATENT DOCUMENTS

| | | | |
|---|---|---|---|
| 1,896,123 | 2/1933 | Schweitzer | 264/19 |
| 2,486,327 | 10/1949 | Rothwell | 264/16 |
| 2,896,265 | 7/1959 | Chambers | 264/17 |
| 2,936,490 | 5/1960 | Mason | 264/19 |
| 3,239,590 | 3/1966 | Trimble | 264/226 |
| 3,446,875 | 5/1969 | Bruckmann | 260/885 |
| 3,905,106 | 9/1975 | Costa et al. | 433/213 |
| 3,917,786 | 11/1975 | Weigert | 264/129 |
| 4,231,830 | 11/1980 | Ryan et al. | 264/226 |
| 4,259,074 | 3/1981 | Link | 433/214 |
| 4,381,918 | 5/1983 | Ehrnford | 433/199 |
| 4,389,496 | 6/1983 | Leusner | 523/109 |
| 4,457,713 | 7/1984 | Schneider | 433/171 |
| 4,500,291 | 2/1985 | Davis | 433/213 |
| 4,542,539 | 9/1985 | Rowe, Jr. et al. | 623/16 |
| 4,552,779 | 11/1985 | McClure | 427/2 |
| 4,556,389 | 12/1985 | Ueno et al. | 433/206 |
| 4,681,543 | 7/1987 | Monroy | 433/196 |
| 4,689,013 | 8/1987 | Lustig | 433/213 X |

Primary Examiner—John J. Wilson
Assistant Examiner—Nicholas D. Lucchesi
Attorney, Agent, or Firm—Richards, Medlock and Andrews

[57] ABSTRACT

A procedure is disclosed for ensuring a uniform thickness in a wax sheet (18) placed over the contoured surface of a preliminary plaster cast (10) in the process of manufacturing dental prosthetics. The sheet (18) has a plurality of uniform diameter spheres (22) distributed throughout the sheet to provide tactile and visual confirmation of uniform thickness. The advantages can also be applied in the manufacture of a custom impression tray (24) or trial denture base or orthopontic retainer (25) of an acrylic material by putting particles of uniform diameter into the acrylic mix. The particles can be precured acrylic which reduces the shrinkage of the acrylic in the tray as it hardens, and maintains the structural and chemical integrity of the finished product as the filler particles chemically incorporate with the powder and liquid mix.

13 Claims, 1 Drawing Sheet

DENTAL MOLDING PROCESS

TECHNICAL FIELD

This invention relates to dental prosthetics, and a method for their preparation.

BACKGROUND OF THE INVENTION

The preparation of partial or full dentures for a patient is a common dental procedure. Albeit common, the preparation of the denture, or removable prosthetic is a very time consuming and skilled procedure.

Typically, the denture preparation begins by placing a soft impression material, typically an algenate, in a stainless steel standard size impression tray. The material and tray are placed in the mouth of the patient to take an initial impression of the mouth and gumline as the patient bites down into algenate material. The algenate material hardens, and is then used to prepare a preliminary plaster cast of the mouth and gum line.

In the subsequent step, a layer of wax material is molded by hand over the contoured surface of the plaster cast, with a great deal of time and skill required to maintain the wax layer at a uniform thickness as it is molded about the often sharp contours of the preliminary plaster cast. Typically, one will experience thin areas in the wax where it passes over ridges on the cast. Overly thick areas of the wax are often encountered where the wax layer passes over valleys in the cast. Maintaining a uniform thickness in the wax layer is critical to the preparation of the prosthetic, especially along the mouth roof contours, and this uniformity is at present achieved only through the careful and time consuming efforts of a skilled practitioner. A custom impression tray is then fabricated over the preliminary plaster cast and wax sheet. The custom impression tray is most typically formed of a two-part acrylic, including a powder and liquid which harden to form the acrylic when mixed together in a certain ratio. Commonly, the liquid and powder are sprinkled together carefully on the wax sheet and preliminary plaster cast to build up the custom impression tray, again hopefully having a uniform thickness.

When the custom impression tray has been formed, the tray is used to form an even more precise final master cast. An acrylic trial denture base is then made from the final master cast. Wax is then built up on the trial denture base and the prosthetic teeth are positioned in the wax. The base, wax and teeth are placed in the patient's mouth and the teeth and wax manipulated to achieve the proper arrangement. The tray, wax and teeth are then put in a mold filled with liquid plaster under pressure. After the plaster has hardened, the wax is melted out of the mold and the base removed. The wax and base are replaced with acrylic under pressure which bonds to the prosthetic teeth to form the final denture which is perfectly fitted to the patient to ensure the patient's comfort and a secure engagement of the denture to the patient's oral tissues.

Because this procedure is so time consuming and requires such a high level of skill, there is a clear imperative to improve the procedure so that it requires less time and less skill while still achieving a quality product.

While the description and claims that follow exemplify processes for fabricating removable prosthetics (dentures and partial dentures), the advantages and claims are equally applicable to the dental discipline of fixed prosthetics (crowns and bridges) where high accuracy impressions are desirable, and orthodontics where removable acrylic appliances, such as retainers, are fabricated on models or casts of the patient's dentition.

SUMMARY OF THE INVENTION

In accordance with one aspect of the present invention, a method is provided for making highly accurate master casts for fabrication of prosthetics for a human mouth. A preliminary plaster cast of the oral tissues of the upper maxillary arch and/or lower mandibular arch is prepared which has a contoured surface closely corresponding to the contours of the oral tissues. The method includes the step of forming a sheet over the contoured surface of the preliminary plaster cast, the sheet including a pliable material and a plurality of filler particles of predetermined diameter. The method further comprises the step of controlling the thickness of the sheet to be uniform over the contoured surface through the presence of the particles, exposure of the filler particles in a first area indicating the sheet is too thin in the first area and covering of the filler particles in a second area so that the particles are non-visible indicating the sheet is too thick in the second area.

In accordance with another aspect of the present invention, the particles can be spheres of nylon having a diameter of about two millimeters, with the pliable material being wax. In accordance with another aspect of the present invention, the particles can be cylinders of nylon having a diameter of about two millimeters with a length about two millimeters.

In accordance with yet another aspect of the present invention, the method can provide for the formation of a custom impression tray by mixing tray filler particles of predetermined diameter with the tray material and thereby controlling the thickness of the tray material to result in a uniform thickness custom impression tray. The material can be a two-part acrylic formed by mixing a powder and liquid.

In accordance with another aspect of the present invention, the method can provide for the formation of a trial denture base or orthodontic retainer by mixing base filler particles of predetermined diameter with the base material, usually a two-part acrylic, to control the thickness of the base.

BRIEF DESCRIPTION OF THE DRAWINGS

Further objects and advantages of the invention will become more apparent from the following description and claims, and from the accompanying drawings, wherein:

DETAILED DESCRIPTION

Figure 1:
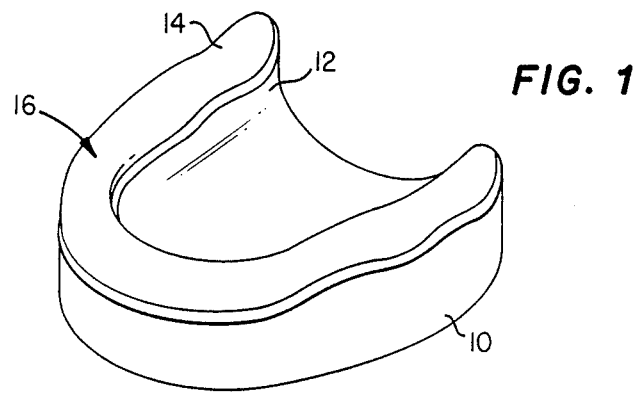
FIG. 1 is a perspective view of a preliminary plaster cast.
Figure 2:
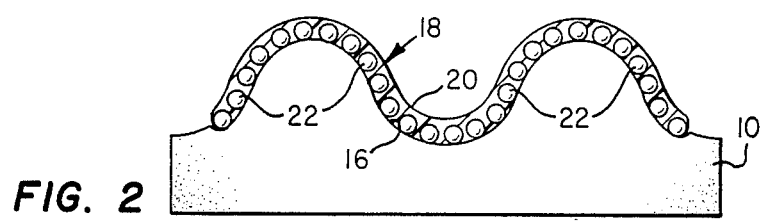
FIG. 2 is a cross sectional view through the preliminary plaster cast illustrating the formation of a uniform thickness sheet over the contoured surface of the plaster cast.
Figure 3:
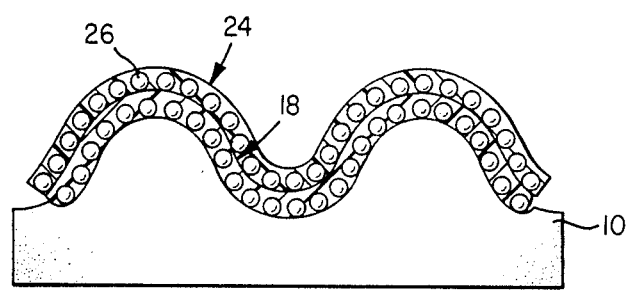
FIG. 3 is a cross sectional view of the preliminary plaster cast illustrating the formation of a custom impression tray of uniform thickness over the preliminary plaster cast and sheet.

With reference to the accompanying FIGS. 1–3, wherein like reference numerals designate like or corresponding parts throughout the several views, the present invention is explained hereinafter.

In the initial stage of preparing a removable prosthetic, specifically a denture or partial denture, a soft impression material, typically an algenate, is placed in a stainless steel standard impression tray. An initial impression of the upper or lower arch and gum line is taken by inserting the stainless steel tray and algenate in the mouth and having the patient bite down into the algenate. For purposes of discussion, the following description and drawings will refer to the process for making a prosthetic for the upper arch and palate. The techniques of the present invention will, however, be usable as well in making a prosthetic for the lower arch or mandible. After the algenate hardens, plaster can be poured into the hardened algenate to form a preliminary plaster cast 10 with contoured surface 16 which has a close approximation of the mouth roof 12 and the gum line 14.

In present procedures, a wax layer is formed over the contoured surface 16 by hand, a time consuming and skilled procedure as discussed previously. In contrast, the present invention contemplates the preparation of a sheet 18 which is formed of wax 20 and a plurality of spheres 22 distributed uniformly within the wax in a single thickness layer. The spheres all preferably have an identical diameter, such as, for example, a diameter of approximately of two millimeters. A sheet 18 can then be formed over the contoured surface 16 of the plaster cast 10. Immediately prior to this step, the wax 20 is preferably heated to make it pliable. The spheres 22 preferably are made of a material with a higher melting point, to retain their diameter dimension as the wax is heated. The spheres can also act as heat sinks for the wax to better distribute the heat applied. The sheet 18 can then be laid on the plaster cast 10 and manipulated to closely follow the contour 16. The user can maintain the desired uniform thickness in the sheet 18 by tactilely and visually observing the spheres 22. If a sphere becomes exposed in a particular area, it is clear that area is too thin, and wax can be taken from a thicker area of the sheet or from another sheet to build up the area. Conversely, as the wax will generally be somewhat translucent, the user will know that the sheet is too thick if a sphere disappears altogether from sight. Of course, wax can then be removed from the thick area until the desired thickness is reached.

In commercial form, the sheets 18 should be manufactured with the spheres uniformly distributed through the wax, and the sheets then packaged in boxes of flat sheets. If desired, a range of sheet thicknesses can be provided. Further, while the filler material has been identified as spheres 22, it will be clear that many other shapes, such as a cylindrical shape of predetermined diameter, can be used to provide the same indication as spheres 22.

After the sheet 18 has been formed over the surface 16, the next step in the prosthetic manufacture is to prepare a custom impression tray 24. The custom impression tray 24 is most typically fabricated out of an acrylic over the preliminary plaster cast 10 and the sheet 18. The sheet 18 provides space for the final impression material to be put on the custom impression tray.

The acrylic is typically supplied in a two-part form, a powder and liquid, which must be mixed in a predetermined ratio to form the acrylic. As previously mentioned, the standard practice today is to carefully sprinkle the powder and liquid on to the wax sheet and preliminary plaster cast until a custom impression tray of sufficient thickness has been built up. This common practice can be continued while using the benefits of the invention described hereinabove. However, even more efficiency can be achieved by incorporating spheres 26 having a predetermined diameter with the acrylic to provide a guide to control the thickness of the acrylic when forming the custom impression tray 24.

Preferably, the spheres 26 will be premixed with the powder. When ready for application, the appropriate quantity of premixed powder and spheres and liquid can be mixed in a tray to achieve a doughlike consistency. The mixture can then be press applied and thinned onto the sheet 18 as shown in FIG. 3 with the spheres 26 acting as a control to maintain a minimum and optimum thickness as the acrylic material is spread to form the tray 24. Again, these spheres 26 can be replaced by cylinders or other shapes as desired as long as the filler material provides the necessary guidance to maintain a uniform thickness in the tray 24.

The spheres 26 can be made of any material suitable for this purpose. However, spheres of precured acrylic are preferred as they would reduce polymerization shrinkage of the powder and liquid as the acrylic hardens to maintain dimensional control, and provide yet another advantage over the present procedure. A cost advantage can be achieved if the spheres 26 are not of acrylic. As acrylic is typically an expensive material for example costing about $30.00/lb. at present prices, a less expensive material can be used in spheres 26 to reduce material costs in the formation of the custom impression tray 24.

Figure 4:
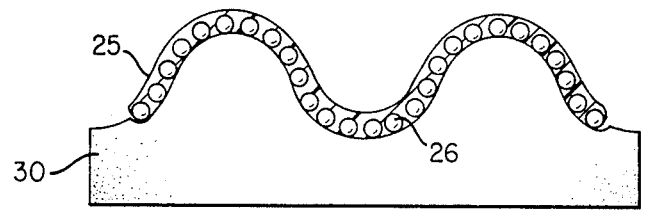
FIG. 4 is a cross sectional view through a final master cast illustrating the formation of a uniform thickness trial denture base over the contoured surface of the master cast.

With reference now to FIG. 4, the advantages of the present invention can be further utilized to make the trial denture base 25 on the final master cast 30. As introduction, the custom impression tray 24 is used to take a more accurate impression of the mouth and gum line than possible with the standard impression tray, achieving dimensions accurate to thousands of an inch, rather than the tens or hundredths of an inch achieved by use of the standard impression tray. The impression formed with custom impression tray 24 is then used to form final master cast 30.

When final master cast 30 is made, the trial denture base 25, usually made of acrylic, is then built up on the contoured surface of cast 30 to a uniform thickness. Spheres 26 are preferably mixed into the powder used to make base 25 with the thickness thereby controlled in the same manner as discussed previously with respect to tray 24. Once base 25 is formed, wax can be built upon the base and the prosthetic teeth fitted to the patient. Since base 25 is quite similar to a removable acrylic appliance (retainer) of the type commonly used to correct teeth misalignment in children (i.e., braces), an acrylic retainer can be made the same way as base 25 using the techniques of the present invention to maintain a uniform thickness in the retainer.

In addition to the uses above, dimensional control spheres can be used in the final retainer product itself, typically formed of polymethyl methacrylate.

While the description above and the claims that follow exemplify processes for fabricating removable prosthetics (dentures and partial dentures), the advantages and claims are equally applicable to the dental discipline of fixed prosthetics (crowns and bridges) where high accuracy impressions are desirable, and orthodontics where removable acrylic appliances, such as retainers, are fabricated on models or casts of the patient's dentition.

While one embodiment of the present invention has been illustrated in accompanying drawings and described in the foregoing Detailed Description, it will be understood that the invention is not limited to the embodiment disclosed, but is capable of numerous rearrangements, modifications and substitutions of parts and elements without departing from the scope and spirit of the invention.

I claim:

1. A method for making a removable prosthetic for the human mouth, the mouth having irregular contours and a gum line, the method including the preparation of a preliminary plaster cast of the contours and gum line, the method comprising the steps of:

forming a sheet over the contoured surface of the preliminary plaster cast, the sheet including a pliable material and a filler comprising a plurality of particles of predetermined diameter;

using the particles to determine the thickness of the sheet over the contoured surface of the plaster cast, exposure of a particle in a first area indicating the sheet is too thin in the first area, covering of a particle in a second area indicating the sheet is too thick in the second area.

2. The method of claim 1 further comprising the step of forming a custom impression tray over the sheet and preliminary plaster cast, the tray being formed of an acrylic material formed by mixing a powder and liquid, the method further comprising the step of mixing the powder and liquid with a plurality of second particles of predetermined diameter to form a mix and placing the mix on the sheet and plaster cast to form the custom impression tray;

using the second particles to determine the thickness of the custom impression tray, exposure of the second particles in a first area of the tray indicating the tray is too thin in the first area, covering of the second particles in the tray in a second area indicating that the second area is too thick.

3. The method of claim 1 further comprising the step of forming the sheet with wax and the particles comprising spheres having a diameter of about two millimeters.

4. The method of claim 3 further comprising the step of forming the spheres out of nylon.

5. The method of claim 1 further comprising the step of forming the sheet out of wax, the particles having a cylindrical shape of diameter approximately two millimeters.

6. The method of claim 1 wherein a trial denture base is formed over a final master cast, the base being formed of an acrylic material formed by mixing a powder and liquid, the method further comprising the step of mixing the powder and liquid with a plurality of second particles of predetermined diameter to form a mix and placing the mix on the final master cast to form the trial denture base; and using the second particles to determine the thickness of the trial denture base, exposure of the second particles in a first area of the tray indicating the tray is too thin in the first area, covering of the second particles in the tray in a second area indicating that the second area is too thick.

7. A method for making a removable prosthetic for the human mouth, the mouth having irregular contours and a gumline, the method including the preparation of a preliminary plaster cast of the contours and gumline and formation of a wax layer over the cast, the method comprising the steps of:

forming a custom impression tray over the wax layer and preliminary plaster cast, the tray being formed of an acrylic material formed by mixing a powder and liquid, the method further comprising the step of mixing the powder and liquid with a plurality of particles of predetermined diameter to form a mix and placing the mix on the plaster cast to form the custom impression tray; and using the particles to determine the thickness of the custom impression tray, exposure of the particles in a first area of the tray indicating the tray is too thin in the first area, covering of the particles in the tray in a second area indicating that the second area is too thick.

8. The method of claim 7 further comprising the step of forming the tray with particles comprising spheres having a diameter of about 2 millimeters.

9. The method of claim 7 further comprising the step of forming the particles of spheres of nylon.

10. The method of claim 7 further comprising the step of forming the particles in a cylindrical shape with a diameter of approximately 2 millimeters.

11. The method of claim 7 further comprising the step of forming a trial denture base over a final master cast, the trial denture base being formed of an acrylic material formed by mixing a powder and liquid, the method further comprising the step of mixing the powder and liquid with a plurality of the particles of predetermined diameter to form a mix and placing the mix on the final master cast to form the trial denture base; and using the particles to determine the thickness of the trial denture base, exposure of the particles in a first area of the trial denture base indicating the trial denture base is too thin in the first area, covering of the particles in the trial denture base in a second area indicating that the second area is too thick.

12. A method for making a removable prosthetic for the human mouth, the mouth having irregular contours and gum line, the method including the preparation of a final master cast of the contours and gum line, the method comprising the steps of:

forming a trial denture base over the final master cast, the trial denture base being formed of an acrylic material formed by mixing a powder and liquid, mixing the powder and liquid with a plurality of particles of predetermined diameter to form a mix;

placing the mix on the final master cast;

using the particles to determine the thickness of the trial denture base, exposure of the particles in a first area of the trial denture base indicating the trial denture base is too thin in the first area, covering of the particles in the trial denture base in a second area indicating that the second area is too thick.

13. A method for making a removable prosthetic for human mouth, the mouth having irregular contours and a gum line, the method comprising the steps of:

(a) preparing a preliminary plaster cast of the contours and gum line;

(b) forming a sheet over the contoured surface of the preliminary plaster cast, the sheet including a pliable material and a filler comprising a plurality of particles of predetermined diameter;

(c) determining the proper thickness of the sheet over the contoured surface of the plaster cast by observing the visibility of the particles within the pliable material;

(d) adjusting the thickness of the sheet by observing a visibility or protuberance of a particle in an area of inappropriate thinness of the sheet, then correcting the thinness, and also by observing a non-visibility or overlap of a particle in an area of inappropriate heaviness of the sheet, then correcting the heaviness.

* * * * *